(12) United States Patent
De Stefanis et al.

(10) Patent No.: US 7,030,285 B2
(45) Date of Patent: Apr. 18, 2006

(54) ALKYLATION PROCESS

(75) Inventors: Adriana De Stefanis, Monterotondo (IT); Giorgio Perez, Rome (IT); Anthony Tomlinson, Monterotondo (IT); Christer Bergström, Espoo (FI)

(73) Assignee: Optatech Corporation, Espoo (FI)

( * ) Notice: Subject to any disclaimer, the term of this patent is extended or adjusted under 35 U.S.C. 154(b) by 507 days.

(21) Appl. No.: 10/182,063

(22) PCT Filed: Jan. 29, 2001

(86) PCT No.: PCT/FI01/00085

§ 371 (c)(1), (2), (4) Date: Jul. 24, 2002

(87) PCT Pub. No.: WO01/55061

PCT Pub. Date: Aug. 2, 2001

(65) Prior Publication Data

US 2003/0023124 A1 Jan. 30, 2003

(30) Foreign Application Priority Data

Jan. 28, 2000 (FI) .................... 20000183

(51) Int. Cl.
*C07C 2/64* (2006.01)
*C07C 2/66* (2006.01)

(52) U.S. Cl. .............. 585/446; 585/435; 585/438; 585/452; 585/453; 585/455; 585/456; 585/467; 585/468

(58) Field of Classification Search ............... 585/435, 585/438, 446, 452, 453, 455, 456, 467, 468
See application file for complete search history.

(56) References Cited

U.S. PATENT DOCUMENTS

| 4,193,454 A | 3/1980 | Goldstein ............. 166/302 |
| 5,097,088 A | 3/1992 | Fukao et al. ............ 585/453 |
| 5,171,896 A | 12/1992 | Knifton et al. ............ 568/791 |
| 5,414,185 A | 5/1995 | Salem et al. ............. 585/721 |
| 6,335,405 B1 | 1/2002 | Okuda et al. ............ 526/161 |

FOREIGN PATENT DOCUMENTS

| EP | 0 558 847 | 9/1993 |
| EP | 0 636 597 | 2/1995 |
| EP | 0 962 470 | 12/1999 |
| EP | 0 985 685 | 3/2000 |
| GB | 2 059 408 | 4/1981 |
| JP | 1061310 | 9/1999 |
| WO | 97/24305 | 7/1997 |

OTHER PUBLICATIONS

Reactive & Functional Polymers 32 (1997) 93-115, "Industrial application of acid-treated clays as catalysts", S.R. Chitnis et al., no month.

*Primary Examiner*—Elizabeth D. Wood
(74) *Attorney, Agent, or Firm*—Cohen, Pontani, Lieberman & Pavane

(57) ABSTRACT

A side-chain of a substituted aromatic compound is alkylated by reacting the aromatic compound with an alkylating agent in the presence of a catalyst. The catalyst comprises a restructured smectite clay to which basic ions are incorporated by ion-exchange. The restructuring of the smectite clay is carried out by acid-treating the clay prior to ion-exchange.

17 Claims, 5 Drawing Sheets

ALKYLATION PROCESS

PRIORITY CLAIM

This is a U.S. national stage of application No. PCT/FI01/00085 filed on 29 Jan. 2001. Priority is claimed on that application and on the following application: Country: Finland, Application No. 20000183, Filed: 28 Jan. 2000.

BACKGROUND OF THE INVENTION

1. Field of the Invention

The present invention relates to alkylation or alkenylation of the side chain of substituted aromatic compounds. In particular, the present invention comprises a process for alkylating the side-chain of xylene with a $C_4$-alkylene or diene.

The present invention also relates to a novel catalyst comprising a restructured clay.

2. Description of Related Art

The alkylation (or alkenylation) of side-chain(s) of alkyl-substituted aromatic hydrocarbons by aliphatic olefins is carried out in the presence of a basic catalyst. An acidic substance, on the other hand, catalyses the alkylation of the benzene ring. Typically, the alkylation reaction is carried out batch-wise or in a fixed-bed reactor in at moderate to high temperatures. In the batch reactor the catalyst is usually present as a slurry.

In prior art, the basic catalysts have typically comprised an alkali metal, optionally on a carrier. Sodium and potassium are the most widely used alkali metals (e.g. H. Pines, J.A.C.S., 1955, 77, 5), and the most typical carriers have been magnesia and alumina, although early examples of the catalysts used for side-chain alkylation include sodium-loaded potassium phosphate (U.S. Pat. No. 5,347,062). U.S. Pat. No. 5,118,895 discloses a catalyst comprising potassium on magnesia and U.S. Pat. No. 5,097,088 discloses a catalyst comprising potassium on magnesia-alumina.

The obvious problem with using metallic alkali metals is their reactivity. It is generally known that alkali metals react vigorously with even small amounts of water. Thus, the use of metallic metal catalysts in an industrial scale process sets very strict requirements to the handling of the starting materials and process operation.

Alumina is useful as a carrier due to its high surface area enabling a good dispersability of the loaded metal. Nevertheless, because of the acidic nature of the alumina, a catalyst comprising conventionally produced alumina as a carrier cannot provide sufficient activity for alkylating the side-chain of aromatic compounds.

On the contrary, a high activity is achieved when a catalyst comprising an alkali metal loaded on a basic carrier is used. For example, alkali-metal impregnated on supports such as Na-exchanged zeolite have been suggested in prior art, but the yields of alkylated product remained extremely low. Thus, the activity of basic catalysts does not result in high yields of reaction products. It can thus be concluded that the basic carriers used to date have been of low surface area and the alkali metal loaded on them is not sufficiently dispersed.

Further, when the catalyst is active enough, problems of a different kind may occur. For example, if the alkylbenzene which is alkylated has more than one side-chain, it is probable that both these side-chains are alkylated—via continued reaction of the alkylating agent present with initial reaction product formed. In some cases the desired product must be removed from the catalyst.

An attempt has previously (U.S. Pat. No. 4,990,717) been made to solve the problem by using both stirred tank and catalytic distillation with fixed catalyst bed, and separating mono-alkenylated product generated from unreacted alkylbenzene and/or C4 to C5 conjugated diene present, both up-stream or downstream. Unreacted alkylbenzene and conjugated diene obtained could then be recycled to the catalyst bed for further alkenylation.

Smectite clays in pillared form have previously been disclosed in Italian Patent Application No. RM 98A 000130. The publication discloses the preparation of catalysts comprising pillared smectite clays to which metal ions have been exchanged. These catalysts are used for catalysing dehydrogenation and in the alkylation reaction of benzene rings.

SUMMARY OF THE INVENTION

It is an object of the present invention to eliminate the problems of prior art and to provide a novel process for alkylating or alkenylating the side-chain of a substituted aromatic compound.

This, and other objects together with the advantages thereof, are achieved by the present invention as hereinafter described and claimed.

The invention is based on the finding that by using a catalyst comprising a restructured smectite clay the side-chain of substituted aromatic compounds can be alkylated or alkenylated. The smectite clay is restructured by treating the clay with an acid, whereupon basic ions are incorporated in the restructured smectite clay by ion-exchange.

The invention also provides novel catalysts comprising restructured clay, which has been subjected to acid-treatment and ion-exchange.

A number of considerable advantages are obtained with the aid of the present invention. The catalyst used in the present process is easy to handle. There are no safety precautions relating to the use of the present catalyst. Further, since there are no noxious substances in the catalyst as such, the catalyst can easily be disposed of after reaching the end of its utility in the present process.

The activity of the catalyst in base-catalysed reactions is sufficiently high. The present catalyst is particularly advantageous in the side-chain alkylation or alkenylation of substituted aromatic compounds, where a catalyst with an even higher activity may give rise to a number of undesired by-products. The yields of the desired products, on the other hand, are distinctly higher than by using catalysts known in the art.

When using the present process in the alkylation of the side-chain, by-products, which may also have use in other applications are formed. Tolyl aldehyde and octatrienal are essentially always formed, even in a relatively high yield of 5–30%, in particular 15–25%, and more than 10%, in particular more than 30%, respectively.

When alkylating the side-chain of xylene with butene or butadiene, the product is more pure than that obtained with conventional methods, thus facilitating further processing by eliminating purification steps. Pure 2-methyl-p-tolyl-butene (or -ane) obtained from the reaction between p-xylene and butene or butadiene can be used, e.g., for producing 2,6-dimethylnaphthalene (disclosed in our co-pending application FI 982630). In this kind of process the purity of the raw material, i.e., the product obtained by the present invention, needs to be as high as possible.

The present process allows for using lower reaction temperatures in a side-chain alkylation reaction than is taught in prior art. The present process also renders it possible to operate at ambient pressure. The possibility of using low temperatures results in more economical production and the low pressure reduces safety risks in an industrial scale process.

DETAILED DESCRIPTION OF THE INVENTION

Definitions

Figure 1:
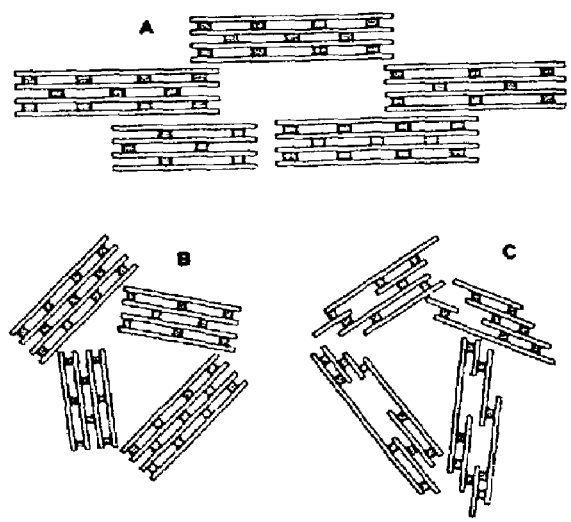
FIG. 1 illustrates the effect of pillaring on a smectite clay.

Generally, "alkylation" is used to designate the reaction in which an alkyl chain is added to a compound, and "alkenylation" refers to a reaction in which an alkenyl chain is added to a compound. It is obvious that the alkylating agent is an alkene while dienes are used as alkenylating agents. For reasons of simplicity, in the following description the term alkylation is used in connections where both reactions are possible. It is to be understood that the used term is intended to cover both reactions.

"Restructured" catalyst means a catalyst treated so that its structure is altered. In the case of smectite clays this can be done by pillaring, i.e., by introducing for example oxidic particles between the layers of the layered smectite clay structure. Another alternative is to treat the smectite clay with acid. The acid-treated catalysts are referred to by a prefix "H" as compared to the untreated smectite clay, for example, MO and H-MO are used to designate untreated montmorillonite and acid-treated montmorillonite, respectively.

The catalyst

The catalyst according to the present invention consists essentially of a restructured clay, preferably a smectite clay, to which basic ions are incorporated by ion-exchange.

The smectite clays are earth-based raw materials, and examples of smectite clay types include montmorillonite (hereinafter MO), beidellite (B), saponite, bentonite, and mixtures thereof, such as beidellite/montmorillonite (Zenith-N, also referred to as ZN). In the present process the catalysts preferably comprise montmorillonite, in particular Texas white montmorillonite and European white montmorillonites (such a Altonit EF White). Smectite clay catalysts are described in U.S. Pat. Nos. 6,335,405, 5,171,896, and 5,414,185.

Smectite clays are highly acidic, and they contain $AlO_4$ and $SiO_4$ tetrahedra and small amounts $MgO$ and $Fe_2O_4$. As an example, the chemical formula of commercial clay Zenith-N is: $(Na_{0.63}K_{0.07} Ca_{0.011})[Si_{7.75} Al_{0.25}] \times (Al_{3.21} Mg_{0.69} Fe_{0.02} Fe_{0.03} Ti_{0.05})O_{20}(OH)_4$.

Smectite clays have platelet morphologies of varying c-order, i.e., with varying number of platelets stacked on one another. The catalysts used in the process of the present invention are, as already discussed, restructured. In the following, two different ways of restructuring the catalysts are discussed:

According to one embodiment of the invention, the smectite clays are pillared with oxidic particles. These compounds are generally known as PILC's. Any smectite clay type can be pillared with oxidic particles in order to form a PILC. The pillaring can be carried out with, e.g., polyhydroxyaluminium-ion-containing solution. Thus, the oxide nanoparticles between the layers of the smectite structure are typically alumina. Hence, the abbreviation "AlZN" refers to a Zenith-N type smectite clay pillared with alumina nanoparticles. The presence of iron in alumina pillars in pillared clays (e.g. FAZA) seems to give rise to the highest amounts of undesirable alkylation side-products.

The effect of pillaring on the structure of the smectite clay is illustrated in FIG. 1. The nano-particles used for pillaring are located between the layers in a smectite clay structure. The nano-particles are then cross-linked, which leads to platelet scission.

Pillared smectite clays and process for the preparation thereof are disclosed, e.g., in Italian Patent Application No. 98A 000130.

Figure 2:
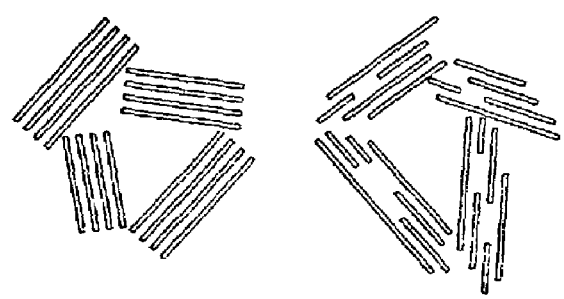
FIG. 2 illustrates the effect of acid-treatment on a smectite clay.

According to another embodiment of the present invention the smectite clays are restructured by acid-treatment. The acid treatment is carried out by bringing the smectite clay into contact with an acid and washing it subsequently with deionized water. The acid for acid-treatment is selected from a group comprising nitric acid, sulphuric acid or hydrochloric acid in aqueous solution. The acid-treatment according to the present invention is mild. The mild acid-treatment means that the concentration of the acid in the solution is $0.1-5$ mol/dm$^3$, preferably $1-2$ mol/dm$^3$, and does not lead to completely disrupt platelet association. This can also be seen in FIG. 2, where the effect of acid-treatment on a smectite clay structure is illustrated.

The acid-treatment is typically carried out at room temperature, but it is also possible to use temperatures in the range of 20–50° C. The acid-treatment lasts typically at least for 1 hour, preferably for at least 3 hours. Preferably, the acid-treatment is carried out under stirring. After having been contacted with the acidic solution, the pH of the smectite clay is typically in the range of 0.1–4, in particular 0.5–2.

The subsequent washing is continued until the pH of the smectite clay is 4.5 or more, preferably 5 or more and in particular 5.5 or more.

Figure 3:
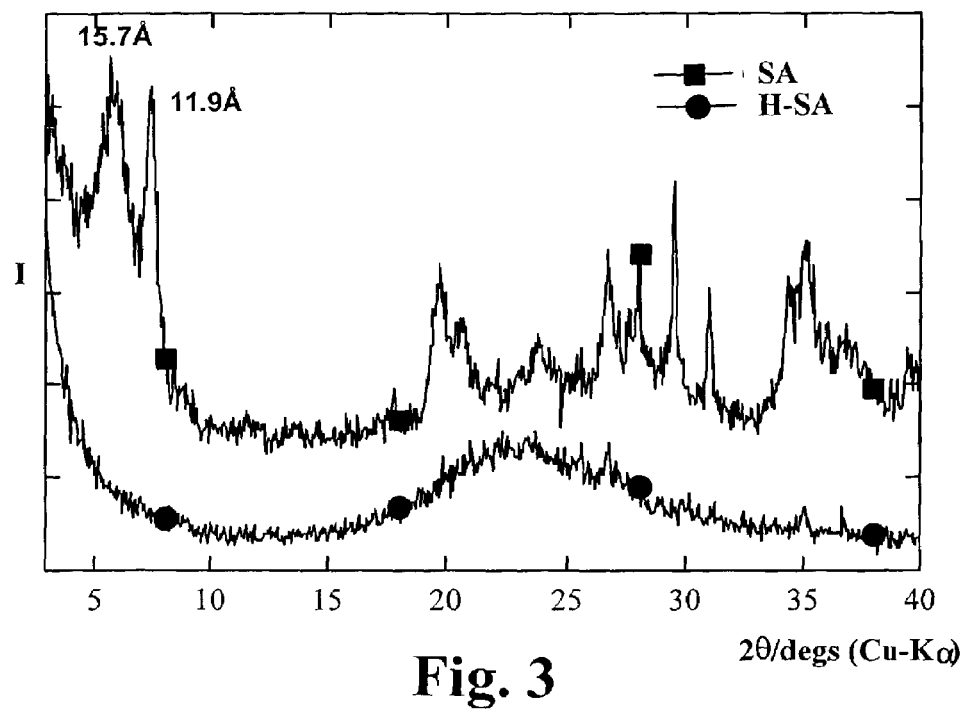
In FIG. 3 is shown an XRPD diagram for saponite and acid-treated saponite.

The catalysts can be characterised by standard techniques, such as X-ray powder diffraction technique and atomic absorption analysis. FIG. 3 shows an XRPD diagram of acid-treated saponite (H-SA) compared with starting saponite (SA). The change of order can be noticed in FIG. 3.

In both of the methods of restructuring presented above, an open, highly porous structure is obtained for the smectite clay. The pores in the structure have openings which are large enough for allowing the reactants and reaction products of the alkenylation reaction pass through.

The smectite clay used in either of the above-described embodiments is preferably finely divided to enable a more complete acid treatment. Optionally, the smectite clay is ground e.g. in a mortar in order to reduce the particle size, and/or it is sieved so as to confirm a relatively homogeneous particle size. It is also possible to reduce the particle size after restructuring by these processes.

The basic nature of the catalyst is achieved by ion-exchange. Thus, the restructured catalyst is subjected to ion-exchange with alkali metal cations, preferably $Na^+$ and/or $K^+$, or alkaline earth metal cations, preferably $Ca^{2+}$, $Mg^{2+}$ and/or $Ba^{2+}$. The exchange level may vary depending on the desired level of basicity and on the size and degree of basicity of the exchanged cation from 0.1 to 30% (w/w), preferably from 0.25 to 20% (w/w) and in particular 8–15% (w/w).

According to one embodiment of the invention, the catalyst is back-exchanged, i.e., a further ion-exchange or further ion-exchange is (are) carried out subsequent to the first (second, etc.) ion-exchange. This arrangement enables tailoring the properties of the catalyst to suite the desired reaction even better. The back-exchanged material is in the following referred to as $M_1M_{11}$-Z, wherein $M_1$ is the first-exchanged cation. $M_{11}$ is the cation exchanged subsequently and Z is the starting smectite clay structure.

After ion-exchange, the catalyst is dried in air at a temperature in the range from 15° to 100° C., preferably at room temperature.

The thus obtained catalysts are new and can preferably be used in base-catalysed reactions, in particular in the side-chain alkylation of substituted aromatic compounds.

Figure 4:
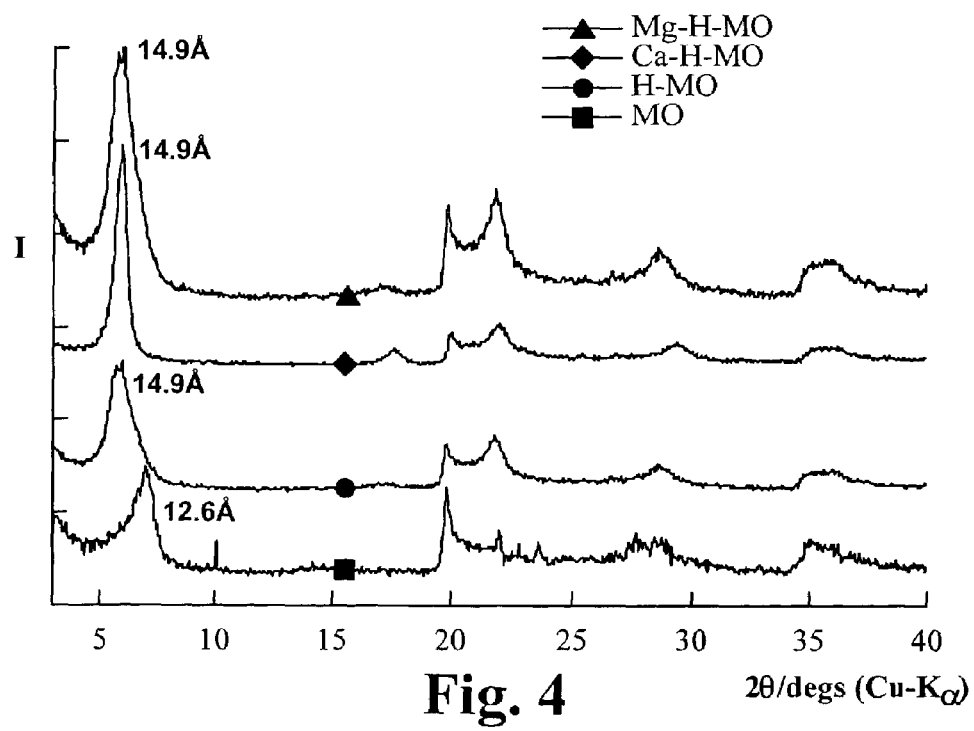
In FIG. 4 is shown an XRPD diagram for montmorillonite, acid-treated montmorillonite, and Ca- and Mg-exchanged acid-treated montmorillonite.

FIG. 4 shows an XRPD diagram comparing the patterns of Texas montmorillonite (MO), acid-treated montmorillonite (H-MO) and $Mg^{2+}$ and $Ca^{2+}$-exchanged acid-treated montmorillonite (Mg—H-MO and Ca—H-MO, respectively).

Prior to its use in an alkylation reaction, the catalyst is activated at a temperature in the range of 50–500° C., preferably 100–250° C., in air. The use of a high activation temperature, i.e., in the range of 250–500° C. results typically in high activity. A drawback is, however, the increasing of the amount of by-products at the same time. Mg—HMO activated at approximately 250° C., however, forms an exception, since the activity is increased without the increase in the amount of by-products.

The Alkylation Process

The process according to the present invention comprises the alkylation of substituted aromatic compounds in the presence of a catalyst comprising a restructured, ion-exchanged smectite clay.

The substituted aromatic compounds typically include alkylbenzenes, in particular alkylbenzenes with a multi-, in particular di-substituted benzene ring. The alkylbenzenes preferably used in the process of the present invention are those having the general formula (I):

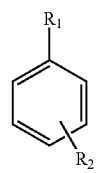

(I)

wherein $R_1$ is methyl, ethyl, propyl, isopropyl, butyl, hydroxyl, $C_1$–$C_3$-aldehyde or amino group, and $R_2$ is hydrogen, linear or branched $C_1$–$C_4$-alkyl-, $C_1$–$C_3$-aldehyde, hydroxyl- or amino group, $R_1$ and $R_2$ being selected so that at least one of the substituents contains at least one carbon atom.

The location of the radicals is preferably such that $R_2$ is in para-position with regard to $R_1$.

Examples of suitable alkylbenzenes include o-, m- and p-xylene, toluene, tolyl aldehyde, aminotoluene, o-, m-, and p-cresol, and phenyl aldehyde. Of these, p-xylene and p-tolyl aldehyde are preferred.

Generally, larger hydrocarbon substituents, having 3 to 4 carbon atoms, are more susceptible to alkylation and alkenylation than substituents with only 1 or 2 carbon atoms. Of the butyl groups, n-, iso- and tert-butyl should be mentioned.

Alkylating agents used in the present invention are selected from the group consisting of ethene, propene, 1- and 2-butene, isobutene and 1,3-butadiene. Of these 1- and 2-butene and 1,3-butadiene are particularly preferred. It is to be noted that the reactivity of alkenes increases when the carbon chain becomes shorter and thus, for ethene and propene, the temperatures used in the process can be set to even lower values.

According to a preferred embodiment of the present invention, the alkylation process comprises the alkylation of xylene, in particular para-xylene, with 1- and/or 2-butene and/or 1,3-butadiene.

According to another preferred embodiment of the present invention the alkylation process comprises the alkylation of tolyl aldehyde with 1- and/or 2-butene and/or 1,3-butadiene.

The process can also be applied to the alkylation of toluene with propylene to yield 2-methylpropyl)benzene which is a useful intermediate for the production of Ibufenac (4-(2-methylpropyl)benzeneacetic acid), Ibuprofen (α-methyl-4-(2-methylprpyl)benzeneacetic acid) and Ibuproxam (N-hydroxy-α-methyl-4-(2-methylpropyl)benzeneacetamide).

Below is shown a reaction equation of the preferred embodiment of the invention. In the equation below $R_1$ is a methyl group and $R_2$ is a methyl or a formyl group in para-position with regard to $R_1$, in other words, the starting material is p-xylene or p-tolyl aldehyde. The alkylating agent is 1- or 2-butene.

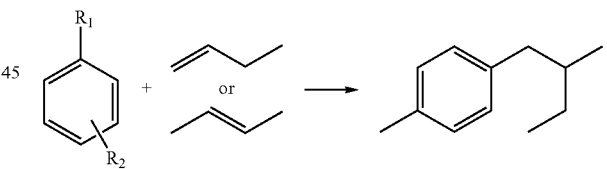

The equation shows that both 1- and 2-butene yield the same compound, i.e., 2-methyl-p-tolyl-butane. Therefore, a mixture of the two compounds can well be used in the alkylation process without a need to product separation. When using 1,3-butadiene in the above reaction, the reaction product has a double bond between the third and fourth carbon atom in the side-chain.

For reasons of simplicity, the reaction products described above are in the context of the present application also referred to as "para-tolyl-pentane or para-tolyl-pentene", both abbreviated "PTP".

The catalyst used in the reaction is described above. Particularly preferred catalyst are $Mg^{2+}$-exchanged catalysts, and in particular $Mg^{2+}$ exchanged montmorillonites.

The alkylation reaction is typically carried out at ambient pressure, but pressures of 0.1–10 bar, preferably 1–5 bar can also be used.

The temperature in the reactors is typically in the range of 150–500° C., preferably in the range of 150–400° C. and in particular in the range of 200–300° C. The use of high reaction temperatures gives rise to the highest activities, but usually also to a larger number of by-products, as a consequence, the preferred reaction temperature for example for Mg—H-MO is approximately 250° C.

Figure 5:
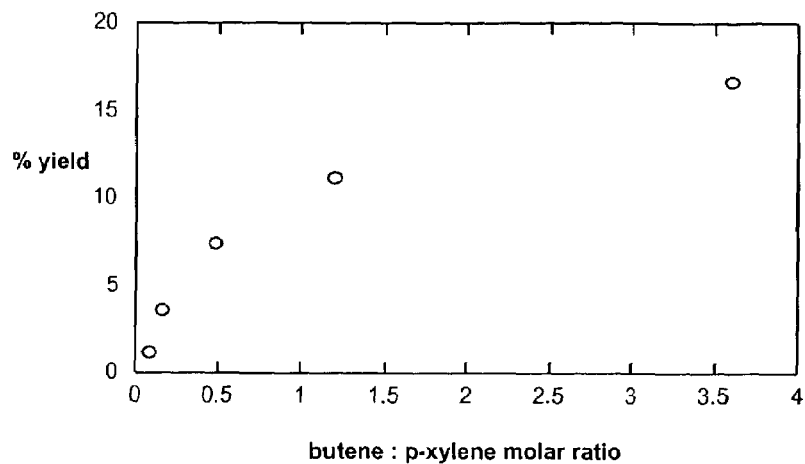
FIG. 5 illustrates the effect of the molar ratio of the starting materials on the yield.

The ratio of the aromatic compound to the alkylating agent is typically kept quite high, in other words, the amount of the alkylating agent with respect to the amount of the aromatic compound in the reactor is low. The low amount of the alkylating agent helps to avoid the polymerisation of the alkylating agent. Typically, the molar ratio of aromatic compound to the alkylating agent is 50 or less, preferably 5 or less and in particular 1. It is, however, also possible to use also greater amounts of alkylating agent, for example in a molar ratio of aromatic compound: alkylating agent of 0.5 or in the range of 0.05–0.005. The effect of the molar ratio is depicted for p-xylene and butene in FIG. 5.

The reaction can be carried out operating in a batch-wise, semi-batch-wise or continuous mode. The reactor can thus be any common stirred-tank reactor or a fixed-bed flow reactor. In the following, each of the three operation modes is presented. As a typical example of the alkylation reaction, and one embodiment of the present invention, the reaction of p-xylene with 1- or 2-butene or 1,3-butadiene is considered.

A. Batch-Wise Operation

The reaction time in the batch- or semi-batch-wise operation is in the range from 1 min to 20 hours. Typically, the reaction time is in the range from 30 min to 8 hours, in particular from 1 to 3 hours.

Yields obtained in a batch-wise operation of p-xylene alkylation with 1- or 2-butene depend on the reaction time and are typically in the range of 0.1 to 30%, preferably 1–20% and in particular 2–17% (calculated with respect to the starting amount of p-xylene).

According to the experiments made on the batch-wise production, a higher pressure in the reactor results in a higher total yield of $C_{12}$-products. Preferably, however, the reaction is carried out at ambient pressure.

B. Semi-Batch-Wise Operation

In the semi-batch-wise mode, the total amount of the substituted aromatic compound is preferably fed to the reactor at the beginning of the reactor operation, and the alkylating agent is fed to the reactor at a predetermined flow rate during the reaction.

The reaction times in the semi-batch operation are similar to those discussed above for the batch-wise operation. At the reaction temperature the reagents and the reaction product are in gaseous phase.

The reactors used in semi-batch-wise operation can be ordinary stirred tank reactors. According to a preferred embodiment of the invention the reaction is carried out in a reflux reactor with circulation. In such an arrangement, the reaction occurs in a reaction zone containing the catalyst. A heating zone comprises typically a vessel or the like and, naturally, means for heating and controlling the temperature. The reagents are preferably fed to the heating zone, which is arranged prior to the reaction zone, and in which the reagent(s) are vaporized. Thus, the reaction occurs in gas phase. As a reactor, an ordinary stirred-tank reactor can be used, but preferably the reactor is a tubular reactor comprising one or several tubes. In a tubular reactor the catalyst is preferably packed to form a bed. The gaseous starting materials react to form reaction products, and the reaction mixture containing these is cooled so that the reaction products and optionally the unreacted starting materials are in liquid phase. The reaction products are optionally recovered prior to feeding the reaction mixture back to the heating zone, where it is, again, gasified.

The substituted aromatic compound is preferably fed to the heating zone in its total amount at the beginning of the reaction operation. The alkylating agent is fed to the reaction mixture, typically to the heating zone, gradually.

Figure 6:
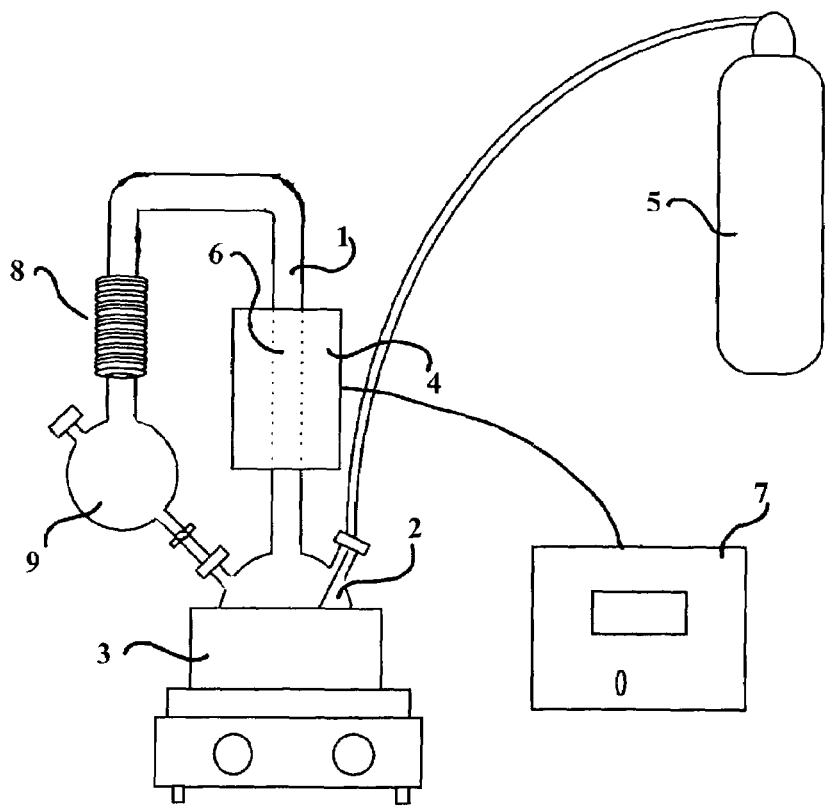
FIG. 6 is a schematic picture of the configuration of a circulatory reflux reactor.

An example of a preferred semi-batch arrangement is shown in FIG. 6. The column 1 in which the reaction occurs is packed with catalyst. The column is typically ade of glass. The column is equipped with means for heating 4, and the reaction zone 6 is the heated part of the column 1. The temperature in the reaction zone 6 is controlled by temperature controlling means 7. The first starting material is fed to the heating zone, in other words, to a round-bottom flask-type recipient 2 located on heater 3. The second starting material is conducted to the recipient 2 located on heater 3. The second starting material is conducted to the recipient 2 continuously or intermittently from a stock container 5. From the reaction zone 6 the gaseous reaction products together with the unreacted starting materials flow to the cooling section, in which the reaction mixture is cooled with means for cooling 8. Optionally, a reservoir 9 is arranged between the cooling section and the heating zone or the reaction zone. Samples of the reaction mixture can be taken from the reservoir 9. The cooled reaction mixture is then conducted back to the recipient 2.

C. Continuous-Flow Operation

In the continuous flow reactors the residence time in the reactor is 1–1000 min, preferably 5–200 min and in particular 10–100 min. The reactor can be an ordinary CSTR, in which the catalyst is placed as such. Preferably, the reactor is a tubular reactor with one or several tubes in which the catalyst is located as a fixed bed.

Figure 7:
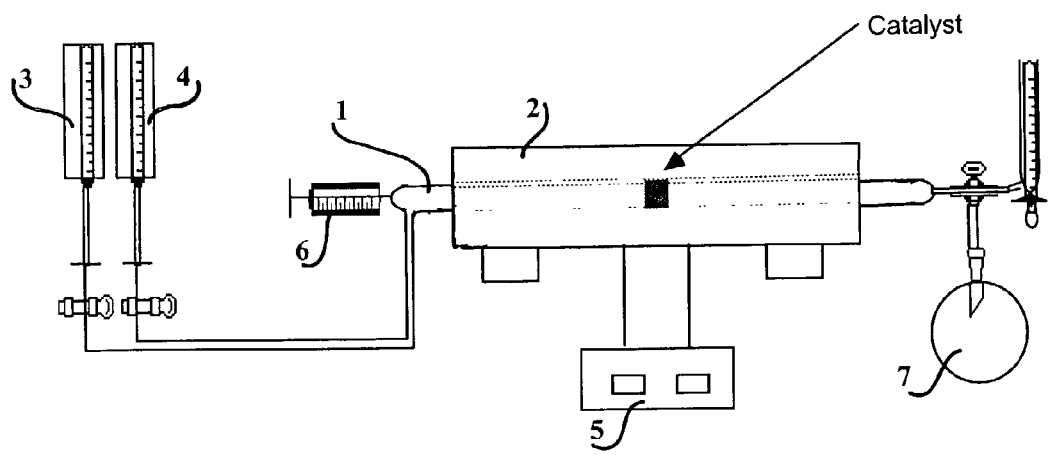
FIG. 7 is a schematic picture of the configuration of a tubular reactor.

An example of a fixed-bed reactor is shown in FIG. 7. Reactor 7 is equipped with means for heating, such as a furnace 2. The temperature in the reactor is controlled by a temperature controller 5. The reactor can be made of any typically used reactor material, for example quartz or steel. The catalyst is located in a fixed bed in the reactor. The catalyst is held in its place by "plugs", which can be selected from such materials that are capable of permitting a gas flow but keeping the catalyst in its place. An inert gas source 3 and a first reagent source 4 are connected to the reactor. The feeding of the second reagent is preferably carried out by using a syringe 6, if the amount of the second reagent to be fed to the reactor is small. The reactor effluent can be collected after reactor 1 to a container 7.

The following non-limiting examples illustrate the present invention in more detail.

EXAMPLE 1

Catalyst Preparation

In the preparation of an acid-treated, ion-exchanged catalyst, the starting clay is acid-treated with 200 ml of 1.25 M HCl/g clay under stirring overnight at room temperature. The sample is then washed with distilled water so as to prepare an acid-treated clay with a pH of 4.5–5. Thereafter, the catalyst is filtered and dried at room temperature in air.

The dried acid-treated catalyst is then exchanged with a group I or II metal cation by contacting 1 g of the restructured clay with 200 ml of a 0.1 M solution of the metal acetate with stirring overnight at 60–80° C. After the exchange the prepared catalyst is filtered, washed with 50 ml of distilled water and dried in air. The exchange procedure is carried out two times.

The starting clay can be any of those described above, for example saponite or montmorillonite. The obtained catalyst can be characterized with XRPD technique. The diagram in FIG. 1 shows the curves of starting Texas montmorillonite, acid-treated montmorillonite and Ca- and Mg-exchanged acid-treated montmorillonite.

SET OF EXAMPLES A

Batch-wise operation

Standard vial procedures were used for estimating catalytic activity under static conditions. In a typical procedure, 10 mg of catalyst was loaded into a tared 10 ml vial attached to a vacuum line and 100 µl of p-xylene containing varying amounts of 1-butene added. In the following, "filling with 300 Torr of 1-butene" means that the pressure of the 1-butene source was 300 Torr (40 kPa). Vials were closed, heated at a pre-fixed temperature for various times, opened and the contents analysed by mass-spectrometry gas chromatograph (GC-MS), the identifications were made by comparison with the NBS data base.

Example A1

Three 10 ml vials were loaded with 10 mg of catalyst prepared according to Example 1, namely Ba—HSA, MgBa—HSA, and Ca—HSA, previously activated at 300° C. for 2 hours, and 100 µl of p-xylene, connected to a vacuum line, evacuated at liquid nitrogen temperature, and, after filling with 300 Torr (40 kPa) of 1-butene, were sealed and allowed to react at 300° C. for 19 h.

The yields of PTP, calculated with respect to initial p-xylene, were 0.25%, 0.35% and 0.50% for Ba—HSA, MgBa—HSA, and Ca—HSA, respectively.

Example A2

Two 10 ml vials were loaded with 10 mg of catalyst prepared according to Example 1, namely MgBa—HSA and Ca—HSA, previously activated at 200° C. for 2 hours, and 100 µl of p-xylene, connected to a vacuum line, evacuated at liquid nitrogen temperature, and, after filling with 300 Torr (40 kPa) of 1-butene, were sealed and allowed to react at 200° C. for 19 h.

The yields of PTP, calculated with respect to initial p-xylene, were 0.02% and 0.02%, for MgBa—HSA and Ca—HSA, respectively.

Example A3

A 10 ml vial was loaded with 10 mg of catalyst prepared according to Example 1, namely Mg—HMO, previously activated at 250° C. for 2 hours, and 100 µl of p-xylene, connected to a vacuum line, evacuated at liquid nitrogen temperature, and, after filling with 30 Torr (4 kPa) of 1-butene, was sealed and allowed to react at 200° C. for 17 h.

The yield of PTP, calculated with respect to initial p-xylene, was 1.60%.

Example A4

A 10 ml vial was loaded with 10 mg of catalyst prepared according to Example 1, namely Mg—HMO, previously activated at 450° C. for 2 hours, and 100 µl of p-xylene, connected to a vacuum line, evacuated at liquid nitrogen temperature, and, after filling with 30 Torr (4 kPa) of 1-butene, was sealed and allowed to react at 150° C. for 17 h.

The yield of PTP, calculated with respect to initial p-xylene, was 0.005%.

Example A5

Two 10 ml vials were each loaded with 10 mg of catalyst, namely Mg—HMO prepared according to Example 1 and NaY, previously activated at 450° C. for 2 hours, and 100 µl of p-xylene, connected to a vacuum line, evacuated at liquid nitrogen temperature, and, after filling with 30 Torr (4 kPa) of 1-butene, were sealed and allowed to react at 200° C. for 2 h.

The yields of PTP, calculated with respect to initial p-xylene, were 0.90% and 0.03%, for Mg—HMO and NaY, respectively.

Example A6

Three 10 ml vials were each loaded with 10 mg of catalyst prepared according to Example 1, namely Mg—HMO, previously activated at 440° C. for 2 hours, and 50 µl of p-xylene, connected to a vacuum line, evacuated at liquid nitrogen temperature, and, after filling with 100, 200 and 300 Torr (13.3, 26.7 and 40 kPa) of 1-butene, were sealed and allowed to react at 320° C. for 16 h.

The yields of PTP, calculated with respect to initial p-xylene, were 1.2%, 3.6% and 7.5%, for the vials filled with 100, 200 and 300 Torr (13.3, 26.7 and 40 kPa) of 1-butene, respectively.

Example A7

A 10 ml vial was loaded with 10 mg of catalyst prepared according to Example 1, namely Mg—HMO, previously activated at 440° C. for 2 hours, and 30 µl of p-xylene, connected to a vacuum line, evacuated at liquid nitrogen temperature, and, after filling with 300 Torr (40 kPa) of 1-butene, were sealed and allowed to react at 320° C. for 16 h.

The yield of PTP, calculated with respect to initial p-xylene, was 11.2%.

Example A8

A 10 vial was loaded with 10 mg of catalyst prepared according to Example 1, namely Mg—HMO, previously activated at 440° C. for 2 hours, and 10 µl of p-xylene, connected to a vacuum line, evacuated at liquid nitrogen temperature, and, after filling with 300 Torr (40 kPa) of 1-butene, was sealed and allowed to react at 320° C. for 16 h.

The yield of PTP, calculated with respect to initial p-xylene, was 16.7%.

Example A9

Four 10 ml vials were loaded with 10 mg of catalyst, namely Mg—HMO prepared according to Example 1, ZnAlZN, NaY, and ZnAlB4, previously activated at 450° C.

for 2 hours, and 100 μl of p-xylene, connected to a vacuum line, evacuated at liquid nitrogen temperature, and, after filling with 15 Torr (2 kPa) of 1-butene, were sealed and allowed to react at 330° C. for 16 h.

The yields of PTP, calculated with respect to 1-butene, were 7.0%, 2.6%, 2.1%, and 0.4% for Mg—HMO, ZnAlZN, NaY, and ZnAlB4, respectively.

Example A10

Two 10 ml vials were loaded with 10 mg of catalyst, namely Mg—HMO prepared according to Example 1, and ZnAlB4, previously activated at 450° C. for 2 hours, and 100 μl of p-xylene, connected to a vacuum line, evacuated at liquid nitrogen temperature, and, after filling with 15 Torr (2 kPa) of 1-butene, were sealed and allowed to react at 380° C. for 16 h.

The yields of PTP, calculated with respect to 1-butene, were 7.0% and 2.0%, for Mg—HMO and ZnAlB4, respectively.

A summary of the results of the above examples A1–A5 is shown in Table 1.

TABLE 1

Reaction of 1-butene and p-xylene.

| Catalyst | Experimental Conditions | Alkylation Products (C12) | Yield % | Example |
|---|---|---|---|---|
| NaY (ª450) | 2h-200° C. 30 mmHg (4 kPa) | 3 | 0.03 | A5 |
| Mg-HMO (450) | 2h-200° C. 30 mmHg (4 kPa) | 4 | 0.9 | A5 |
| Mg-HMO (450) | 17h-150° C. 30 mmHg (4 kPa) | 1 | 0.005 | A4 |
| Mg-HMO (250) | 17h-200° C. 30 mmHg (4 kPa) | 5 | 1.6 | A3 |
| Ca-HSA (200) | 19h-200° C. 300 mmHg (40 kPa) | 1 | 0.02 | A2 |
| MgBa-HSA (200) | 19h-200° C. 300 mmHg (40 kPa) | 1 | 0.02 | A2 |
| Ba-HSA (300) | 19h-300° C. 300 mmHg (40 kPa) | 2 | 0.25 | A1 |
| MgBa-HSA (300) | 19h-300° C. 300 mmHg (40 kPa) | 3 | 0.35 | A1 |
| Ca-HSA (300) | 19h-300° C. 300 mmHg (40 kPa) | 3 | 0.5 | A1 |

ª=activation temperature

The yield is calculated with respect to the initial amount of p-xylene.

Utilising the catalyst Mg—H-MO, a series of experiments was carried out—again in vials, and at 330° C. or (380° C.) for 16 h, in which the p-xylene: 1-butene ratio was kept at 100:1 (wt %). The results are shown in Table 2.

o-tolyl-pentane (OTP) was obtained as a by-product from the reaction of p-xylene and 1-butene at the process conditions described above, when using the same catalyst and a ratio p-xylene: 1-butene=10:3.

TABLE 2

Typical vial catalytic test for Mg—H—MO (10 ml vial, 320° C., 16 h)

| p-xylene (μl) | 1-butene, Torr (kPa) | 1-butene: p-xylene molar ratio | % yield with relation to xylene |
|---|---|---|---|
| 50 | 100 (13.3) | 0.08 | 1.2 |
| 50 | 200 (26.7) | 0.16 | 3.6 |

TABLE 2-continued

Typical vial catalytic test for Mg—H—MO (10 ml vial, 320° C., 16 h)

| p-xylene (μl) | 1-butene, Torr (kPa) | 1-butene: p-xylene molar ratio | % yield with relation to xylene |
|---|---|---|---|
| 50 | 300 (40) | 0.48 | 7.5 |
| 30 | 300 (40) | 1.2 | 11.2 |
| 10 | 300 (40) | 3.6 | 16.7 |

The reaction is preferably even more efficient at higher p-xylene: 1-butene ratios (>500:1) with fewer side reactions. In other words, such a feed should give complete consumption of 1-butene (100% 'yield' with respect to 1-butene), but preferably the reaction would then be carried out at non-static process conditions, such as catalytic distillation.

Figure 8:
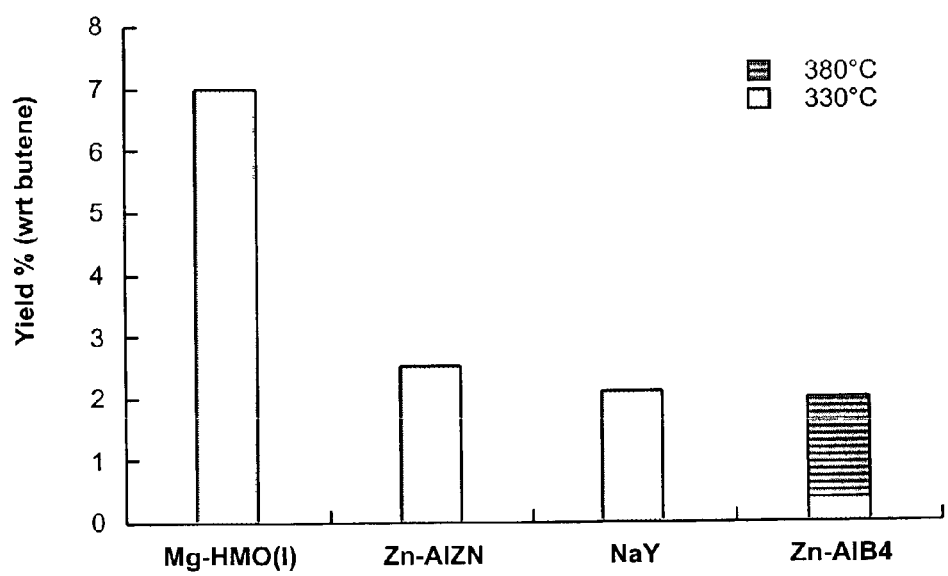
FIG. 8 illustrates the yields in the reaction between p-xylene and 1-butene using four different catalysts.

FIG. 8 illustrates the yields at high p-xylene: 1-butene ratios in static experiments for Mg—HMO, Zn-AlZN, NaY and Zn-AlB4. The reactions were carried out at 330° C., except for Zn-AlB4-catalyst the reaction of which was carried out also at 380° C.

Production of PTP Using Tolyl Aldehyde

Tolyl aldehyde may also be utilised instead of p-xylene, as the substituted aromatic compound of the present process to obtain PTP. A series of vial reactions was carried out, now substituting tolyl aldehyde for p-xylene, and using procedures detailed in Example A2. The product shows a GC peak with a retention time near that of PTP and a yield of >20% (calculated with respect to 1-butene).

Example A11

A 10 ml vial was loaded with 10 mg of catalyst, namely Mg—HMO, previously activated at 440° C. for 2 hours, and 10 μl of p-tolylaldehyde, connected to a vacuum line, evacuated at liquid nitrogen temperature, and, after filling with 15 Torr (2 kPa) of 1-butene, was sealed and allowed to react at 330° C. for 16 h.

The yield of PTP, calculated with respect to 1-butene, was 24%.

Set of Examples B

Semi-Batch-Wise Operation

To further investigate whether 1-butene alone (without catalyst) may be involved in the reaction giving rise to PTP, a series of experiments was performed in which p-xylene and 1-butene were simply refluxed for varying periods of time and the products were analysed using a GC. In a typical run, 1-butene was bubbled (50 ml·h$^{-1}$) through 50 ml of p-xylene in a standard reflux apparatus. Note that this reaction, at this temperature (138° C.), gives rise to measurable quantities of the required final product.

The semi-batch reactor configuration used in the examples below is a circulatory reflux reactor related to catalytic distillation and illustrated in FIG. 6.

The glass column in which the reaction occurs, was packed with 50 mg of Mg—HMO-catalyst. The round-bottom flask-type recipient on the heater was charged with 50 ml dry p-xylene, which was then refluxed under various conditions of 1-butene pressures. The product PTP is collected from the round-bottom-flask. The reservoir collects product as formed and via septum I was used to draw off samples for GC/MS analysis and check when the catalyst utilised is exhausted.

Example B1

The recycling catalytic reactor was filled with 50 mg of Mg—HMO, previously activated at 450° C. for 4 h. The catalyst was heated at 250° C. and p-xylene (50 ml) was heated at its boiling point. A mixture nitrogen/1-butene (100:1) was allowed to bubble into p-xylene at a flow rate of 50 ml h$^{-1}$. After 24 h the yield of PTP, calculated with respect p-xylene, was 0.8%.

Example B2

The recycling catalytic reactor was filled with 50 mg of Mg—HMO, previously activated at 450° C. for 4 h. The catalyst was heated at 250° C. and p-xylene (50 ml) was heated at its boiling point. A mixture nitrogen/1-butene (1:1) was allowed to bubble into p-xylene at a flow rate of 50 ml h$^{-1}$. After 24 h the yield of PTP, calculated with respect p-xylene, was 1.2%.

Example B3

The recycling catalytic reactor was filled with 50 mg of Mg—HMO, previously activated at 450° C. for 4 h. The catalyst was heated at 250° C. and p-xylene (50 ml) was heated at its boiling point. 1-butene was allowed to bubble into p-xylene at a flow rate of 50 ml h$^{-1}$. After 24 h the yield of PTP, calculated with respect p-xylene, was 4.5%.

Example B4

The recycling catalytic reactor was filled with 50 mg of Mg—HMO, previously activated at 450° C. for 4 h. The catalyst was heated by boiling p-xylene (50 ml). A mixture nitrogen/1-butene (10:1) was allowed to bubble into p-xylene at a flow rate of 50 ml h$^{-1}$. After 24 h the yield of PTP, calculated with respect p-xylene, was 0.6%.

Table 3 illustrates the effect of 1-butene pressure on the yield of PTP in a reflux reactor at 250° C. after a reaction time of 24 h.

TABLE 3

The effect of 1-butene pressure on the yield of PTP.

| 1-butene | % yield |
| --- | --- |
| very low (in N$_2$ flow) | 0.8 |
| 0.5 atm (50.7 kPa) (in N$_2$ flow) | 1.2 |
| 1 atm (101 kPa) | 4.5 |

Example C

Continuous Flow Operation

A fixed-bed reactor was set up as shown in FIG. 7. The reactor system used in the experiment below consists of a quartz tube reactor in which the catalyst is charged and held in place by plugs. A septum at one end allows a syringe to be inserted to provide controlled amounts of p-xylene and also to draw off samples for analysis. Controlled amounts of 2-butene are supplied via standard graduated glassware as shown. Product is collected in the reservoir equipped with a flow-meter.

Example C1

The fixed bed reactor was filled with 500 mg of Mg—HMO, heated at 450° C. and activated under nitrogen flow for 2 hours. 5 ml of p-xylene was slowly (1ml/min) injected in the reactor together with a nitrogen/butene (95:5) mixture whose flow rate was 0.1 l/h. The products were collected at the end of reactor and the yield of PTP, calculated with respect to initial p-xylene, was 0.2%.

Example 2

Catalyst Preparation

Altonit EF White (EFW) from IKO-Erbslöh GmbH was used as parent clay in the preparation of the Mg—H-MO and Mg-MO catalysts.

A sample of EFW (20 g starting clay) was treated with 200 ml of 0.05M HCl/g clay under stirring for 3 hours at room temperature. The sample was then decanted and distilled water was added to reach the previous volume regardless of the pH (3÷5). The sample was subsequently exchanged with a group I or II metal acetate by adding 20 mmol of metal acetate per g of restructured clay and stirring overnight at 60–80° C. After the exchange the sample was filtered, washed with 50 ml of distilled water and air dried. The exchange was repeated twice.

The magnesium uptake, as determined by AA, depends on the acid concentration used in restructuring the clay corresponding to a higher acidity a larger uptake. It was in the range 18–14%. When MO was exchanged with magnesium in the absence of acid treatment, with the same procedure reported above, the magnesium uptake was 7.5%.

Figure 9:
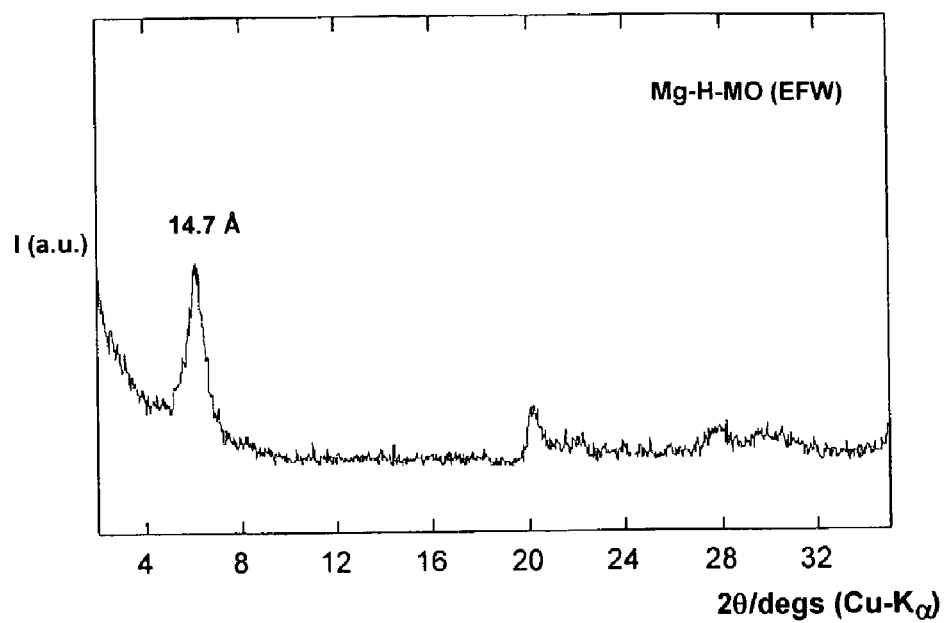
FIG. 9 depicts an X-ray powder diffraction pattern of acid-treated montmorillonite Mg exchanged.

The catalysts were characterized by standard X-ray powder techniques (Ni-filtered, Cu—K$_\alpha$ radiation) and atomic absorption analysis. FIG. 9 shows the XRPD of mild acid-treated EFW (sample 16).

Example D

Four catalysts were prepared using different HCl concentrations in montmorillonite treatment before the magnesium exchange.
Catalyst 1: HCl 0.5 M
Catalyst 2: HCl 0.1 M
Catalyst 3: no acid
Catalyst 4: HCl 0.05 M To compare the catalytic properties of the above 4 catalysts they have been tested in vials following the procedure described above. To a weighed amount (10 mg) of catalyst activated at 440° C., a known amount of p-xylene (100 μl) were added together with 300 torr (40 kPa) of 1-butene, sealed under vacuum, and allowed to react at 280° C. for 16 hours.

The obtained results are shown in Table 4:

TABLE 4

Yield of alkenylation reaction calculated with respect to p-xylene (vials experiments)

| Catalyst | HCl concentration | Yield |
| --- | --- | --- |
| Mg-HMO | 0.1 M | 0.37% |
| Mg-HMO | 0.5 M | 1.03% |
| Mg-HMO | 0.05 M | 6.97% |
| MG-MO | | 2.10% |

The yields of the products are somewhat lower than obtainable with a catalyst derived from Texas montmorillonite, however the reaction product is very clean which provides for the use of a process with continuous or intermittent recirculation of the unreacted reactants to increase the yield.

The invention claimed is:

1. A process for alkylating or alkenylating a side-chain of a substituted aromatic compound, said process comprising
   restructuring a smectite clay by acid-treating or pillaring,
   incorporating basic ions into the restructured smectite clay by ion-exchange, and
   reacting the substituted aromatic compound with one of an alkylating agent and an alkenylating agent in the presence of a catalyst, wherein said catalyst comprises said restructured smectite clay into which said basic ions have been incorporated.

2. The process according to claims 1, wherein the pillared structure comprises oxidic nanoparticles.

3. The process according to claim 1, wherein the ion that is exchanged is selected from the group consisting of alkali metal ions, alkaline earth metal ions and $Zn^{2+}$ ions.

4. The process according to claim 3, wherein the ion that is exchanged is selected from the group of $Na^+$, $K^+$, $Ca^{2+}$, $Mg^{2+}$, $Ba^{2+}$ and $Zn^{2+}$ ions.

5. The process according to claim 1, wherein the smectite clay is selected from the group consisting of saponite, montmorillonite, beidellite, bentonite and mixtures thereof.

6. The process according to claim 1, wherein the catalyst comprises acid-treated montmorilonite exchanged with $Mg^{2+}$ ions.

7. The process according to claim 1, wherein the one of an alkylating agent and an alkenylating agent is an aliphatic unsaturated compound.

8. The process according to claim 7, wherein the one of an alkylating agent and an alkenylating agent is one of a linear and a branched $C_2$–$C_{10}$.

9. The process according to claim 8, wherein the one of an alkylating agent and an alkenylating agent is one of a $C_3$–$C_8$ alkene and a $C_3$–$C_8$ diene.

10. The process according to claim 7, wherein the one of an alkylating agent and an alkenylating agent is one of 1-butene, 2-butene, and 1,3-butadiene.

11. The process according to claim 1, wherein the substituted aromatic compound is an alkylbenzene.

12. The process according to claim 11, wherein the alkylbenzene has the general formula (I)

(I)

wherein
   $R_1$ is one of methyl, ethyl, propyl, isopropyl, butyl, $C_1$–$C_3$-aldehyde, hydroxyl and amino groups, and
   $R_2$ is one of hydrogen, linear $C_1$–$C_4$-alkyl-, branched $C_1$–$C_4$-alkyl-, $C_1$–$C_3$-aldehyde, hydroxyl and amino groups,
   $R_1$ and $R_2$ being selected so that at least one of the substituents contains at least one carbon atom.

13. The process according to claim 12, wherein $R_1$ is a methyl group and $R_2$ is a methyl group.

14. The process according to claim 12, wherein $R_1$ is a methyl group and $R_2$ is a CHO-group.

15. The process according to claim 12, wherein $R_2$ is in para-position with regard to $R_1$.

16. The process according to claim 1, wherein the substituted aromatic compound is p-xylene and the alkylating agent is at least one of 1-butene, 2-butene and 1,3-butadiene.

17. The process according to claim 1, wherein the process is carried out in a reflux reactor with circulation.

* * * * *